United States Patent [19]

Lebeau

[11] Patent Number: 5,204,910
[45] Date of Patent: Apr. 20, 1993

[54] METHOD FOR DETECTION OF DEFECTS LACKING DISTINCT EDGES

[75] Inventor: Christopher J. Lebeau, Tempe, Ariz.

[73] Assignee: Motorola, Inc., Schaumburg, Ill.

[21] Appl. No.: 896,460

[22] Filed: Jun. 8, 1992

Related U.S. Application Data

[63] Continuation of Ser. No. 705,228, May 24, 1991, abandoned.

[51] Int. Cl.[5] .............................................. G06K 9/00
[52] U.S. Cl. ......................................... 382/8; 382/51; 53/55; 358/106
[58] Field of Search ................... 382/8, 18, 19, 20, 51, 382/53, 55; 358/101, 106; 356/237

[56] References Cited

U.S. PATENT DOCUMENTS

| | | | |
|---|---|---|---|
| 4,477,926 | 10/1984 | Linger et al. | 382/8 |
| 4,755,874 | 7/1988 | Esrig et al. | 358/106 |
| 4,760,444 | 7/1988 | Nielson et al. | 358/101 |
| 4,791,586 | 12/1988 | Maeda et al. | 364/491 |
| 4,926,489 | 5/1990 | Danielson et al. | 382/8 |
| 5,023,916 | 6/1991 | Breu | 382/8 |

Primary Examiner—David K. Moore
Assistant Examiner—Andrew W. Johns
Attorney, Agent, or Firm—Joe E. Barbee

[57] ABSTRACT

A method of image processing for visually inspecting a workpiece. The method compares the brightness (15) at each location within an image of the workpiece to the equivalent location within an image of an idealized workpiece. The inspection depends only on local brightness differences between the two images. The method can detect defects which have no distinct edges. Finally this method can detect defects which are small enough that the resolution of the image will show these small defects only as a single point of light (12) or dark (27).

11 Claims, 3 Drawing Sheets

POSITION

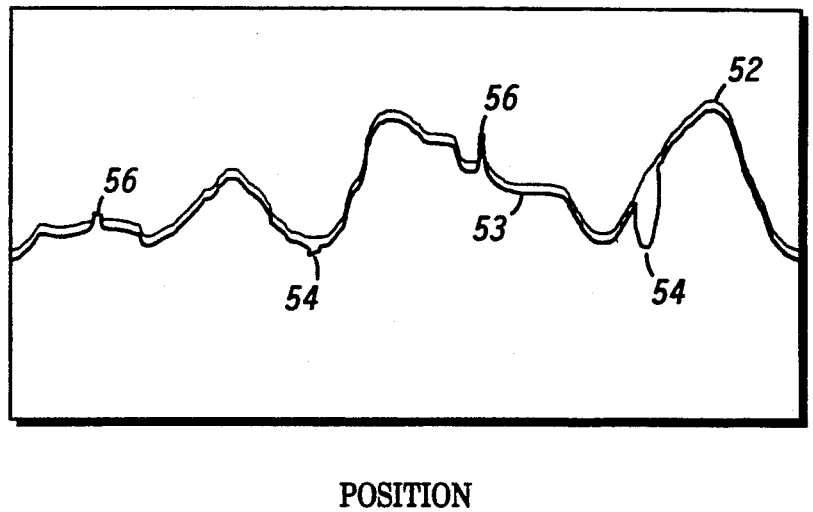
FIG. 10
FIG. 11
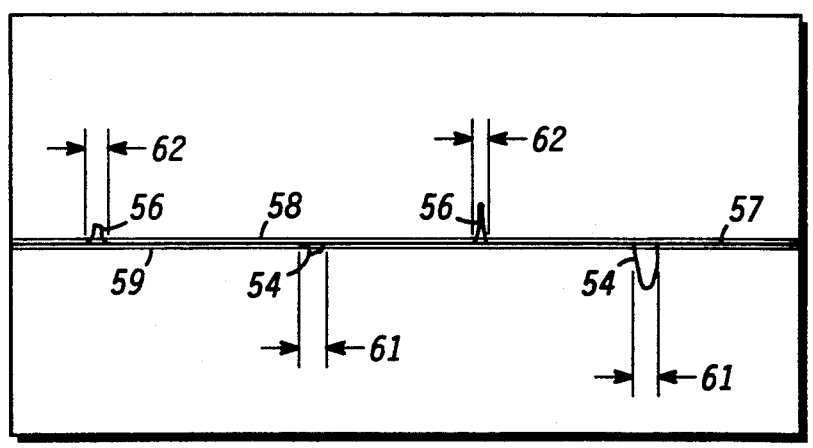

METHOD FOR DETECTION OF DEFECTS LACKING DISTINCT EDGES

This application is a continuation of prior application Ser. No. 07/705,228, filed May 24, 1991, now abandoned.

A relating co-pending patent application by the inventor of the present invention, assigned to the same assignee, is application number 07/533,207, filed Jun. 4, 1990, entitled "Method for Automatic Semiconductor Wafer Inspection".

BACKGROUND OF THE INVENTION

The present invention relates, in general, to inspection of semiconductor wafers, and more particularly to a method of processing images of a patterned workpiece to enhance the inspection process.

Defect density is known to be a major yield limit in semiconductor manufacture and must be monitored to provide data for yield control. Accurate defect density measurements can also be used to predict reliability and lifetime of an integrated circuit. Manual inspection is rather simple and requires relatively low cost equipment, but the results are inconsistent because of the subjective nature of the assessment and the attention span of the operator. Further, the time required to process the wafers as well as the limited amount of information that may be readily obtained limits the application of manual inspection techniques to statistical sampling. In practice, this detection procedure is carried out on only a small percentage of the processed wafers. Such a procedure is grossly inefficient in that 90% or more of the processed circuits are never inspected. Further, as the circuits become more complicated and patterns become smaller, it becomes increasingly difficult to see defects let alone classify such defects. Present methods of integrated circuit inspection provide only estimates of defect density and thus can not fulfill the greater needs of the semiconductor industry.

The semiconductor industry has developed a variety of automatic workpiece inspection systems to fill this need. These systems can inspect all the circuits of many wafers in a time efficient manner, but certain types of defect cannot be detected reliably. One of the basic problems associated with such automation is the methods used to separate defects from the desired patterns on the workpiece. In the past this image processing has been directed to detection, classification and comparison of shape and edge information. The prior art includes many methods based on one or both of these image characteristics. These approaches give good results if there are clear edges to the defect, but is less effective with defects which do not have distinct edges. Defects such as breaks in objects or extraneous particles tend to form distinct edges. As a result these defects are well suited to the detection methods of the prior art. There is another class of defects such as stains, smears and some types of surface scratches which tend to blend into other shapes rather than forming distinct edges. Edge or shape detection is not sufficient for this class of defect. In addition, an edge or shape detection method is highly dependent upon the specific lighting conditions used for inspection. Any change of color, light intensity, or angle of illumination will alter the edges detected in some way. The nature of edge detection also requires that the defect span several pixels to form a detectable edge. This requirement limits the minimum size of defect which can be detected by the use of such methods.

There exists a need for an automated workpiece inspection system which can detect the class of defects having no distinct edges. The system must be sensitive to objects which are as small as one or two pixels, but must be insensitive to lighting conditions during the inspection process.

SUMMARY OF THE INVENTION

Briefly stated, the present invention provides a method of image processing for visually inspecting a workpiece. The method requires an image of the workpiece and an image of an idealized workpiece. The images are processed to refine the effective registration between the images and to compensate for differences in the overall brightness. After processing, the images are compared and localized differences in brightness are recorded as defects. The resulting inspection is insensitive to variations in absolute brightness, depending instead on the brightness differences between small areas of the two images. The method of the present invention can detect gradual changes in surface features having no distinct edges. Finally this method can detect defects which are small enough that the image will show these small defects only as a single point of light or dark.

BRIEF DESCRIPTION OF THE DRAWINGS

FIG. 10 is a representation of two image slices;
and
FIG. 11 is an image slice derived from FIG. 10.

DETAILED DESCRIPTION OF THE DRAWINGS

Figure 1:
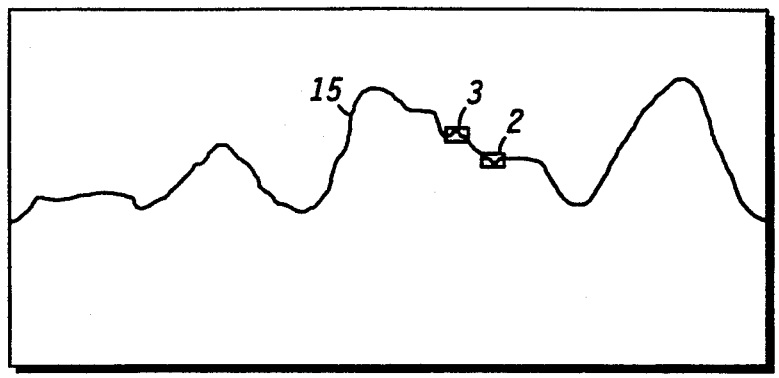
FIG. 1 is a representation of an image slice.

FIG. 1 is a graphical representation of the relative brightness of an image slice across an image of a workpiece. The image slice depicted may be derived either from a taught image or from a run image. The taught image is an image of a defect free workpiece which is used as a standard of comparison for inspection purposes. The run image is an image of a workpiece being inspected by comparison with the taught image. The relative brightness levels across the image slice are shown as a graph of a plurality of graylevels 15. Thus the image slice depicted applies equally to a graylevel representation of a taught image of a workpiece and a graylevel representation of a run image of a workpiece. A section comprising a local dark spot and a plurality of surrounding pixels, enclosed in box 2, is shown in more detail in FIG. 2 below. Similarly a section comprising a local light spot and a plurality of surrounding pixels, enclosed in box 3, is shown in more detail in FIG. 3 below. Graylevels 15 are quantized to depict a specific graylevel value for each image slice element or pixel of the image slice. Graylevels 15 increase linearly with higher image brightness, and decrease linearly with lower image brightness. The image slice depicted is used only for purposes of explanation since the method according to the present invention is typically applied across the entire image without a directional preference. The image slice is only one of many such slices which comprise the complete image, a single scan of a raster scan is an example of one such image slice. The image slice is assumed to be parallel to a horizontal or vertical axis of the image. The workpiece being inspected may be any artifact for which an automated visual inspection is desired. The workpiece may comprise the surface of a semiconductor wafer, a printed circuit board, a mechanical component such as a gear, or a pattern such as a textile weave.

The method according to the present invention comprises a method for performing a detailed comparison of the relative brightness of a taught image with a run image. In order to achieve this comparison the images must be processed to remove variations which are not due to defects. Extraneous variations of this type include differences in overall brightness spatial position, rotation, and magnification. Processing of the taught image and the run image is performed so as to provide a precise matching between the two images which is beyond the capability of the unassisted imaging device. The image processing comprises two major steps: a relaxation to improve image registration, and adjustment of the overall brightness levels of the images. These steps may be performed in any order and may modify, the taught image, the run image, or both. A typical selection of step order and images to be modified is described below as part of a preferred embodiment of this invention.

In the preferred embodiment, a computer is used to store a representation of graylevel 15 as a numeric value in the range of zero to 255 for each pixel. The image is organized in the computer memory as an array of numeric values having 512 horizontal rows and 512 vertical columns. In this preferred embodiment of the invention, the operations described are performed arithmetically according to algorithms well known in the art. Typical algorithms used for this purpose are found in the article: "Tutorial on advances in morphological image processing and analysis", P. Maragos, Optical Engineering, July 1987, Vol. 26 No. 7, Pages 623 through 632. An alternative embodiment of this invention implements the required algorithms using digital hardware. Another embodiment of the present invention uses analog filtering techniques such as low pass filters, bandpass filters, and variable gain amplifiers applied to the analog signal from a video camera. Other embodiments include using well known photographic techniques such as alterations in exposure and development timing, successive contact printing, negative images, and selection of emulsion contrast characteristics.

To compare two images, both images must first be accurately registered with one another. Initial registration is performed by adjustment of the workpiece position and by adjustment of the imaging system optics. In this way the run image is registered by mechanical and optical means to scale, rotation and spatial position of the taught image. It is impractical to register two images to the accuracy of less than a single pixel across the span of a typical workpiece in this way however. Therefore registration between the representations of the images is refined by a relaxation of the graylevel representation of at least one of the two images. This relaxation is achieved by modifying the graylevel representation of the image to enlarge the local dark areas and the local light areas of the representation of the image. In the preferred embodiment of this invention a relaxation of a single pixel around each dark or light spot is used. For example, an image of a single pixel dark point is relaxed so the point covers a disk three pixels in diameter. Comparing this relaxed image with a second image of the same dark point will show the two points as coincident even though the representations of the images do not register exactly. This relaxation may be performed on the taught image, the run image, or both images. To minimize the work involved relaxation is typically performed on the taught image only.

Figure 2:
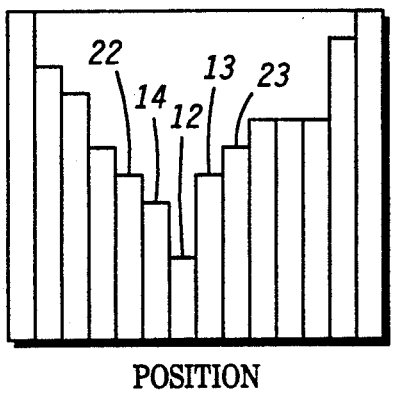
FIG. 2 is an enlargement of a portion of FIG. 1.
Figure 3:
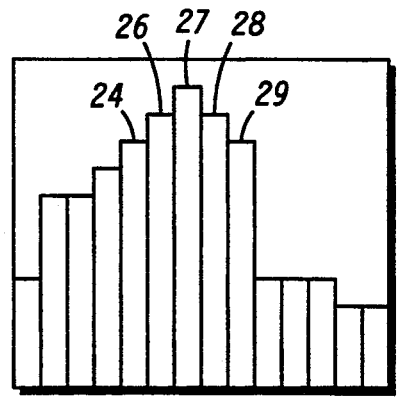
FIG. 3 is an enlargement of another portion of FIG. 1.

FIG. 2 is an enlargement of a portion of the image slice having a local dark spot 2 (FIG. 1). A plurality of pixels in this portion of the image slice have graylevel values depicted as a bar graph. The height of each bar depicts the graylevel value for an individual pixel. A plurality of these bars 22, 14, 13 and 23 depict a region of local darkness in the image slice. Typically the graylevel value for each pixel represents a mean value of brightness within that pixel. A single dark pixel as depicted by bar 12 represents a dark spot that is small enough to span less than a single pixel. In the same fashion, bars 22, 14, 12, 13, and 23 represent areas of increasing brightness in the vicinity of bar 12. Similarly, FIG. 3 is an enlargement of a portion of the image slice depicted in FIG. 1 in the vicinity of a local bright spot 3 (FIG. 1). A plurality of bars 24, 26, 27, 28, and 29 depict a region of local brightness in the image slice. Bar 27 represents the average brightness of a bright point that is small enough to span less than a single pixel. Bars 24, 26, 28, and 29 represent areas which are less bright than bar 27.

Figure 4:
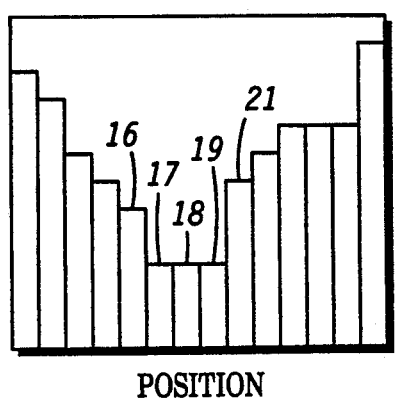
FIG. 4 shows FIG. 2 following an erode operation.

FIG. 4 shows the portion of the image slice depicted in FIG. 2 following a graylevel morphological erosion. The graylevel morphological erosion serves to expand the area of the darkest portions of the representation of the image while preserving the relative brightness of other parts of the representation of the image. This is accomplished by comparing each pixel's graylevel value with that of its immediate neighbors. The lowest graylevel value in the area of inspection becomes the graylevel value of the pixel. The graylevel morphological erosion may cover a small area of the representation of the image or may inspect an arbitrarily large area of the representation of the image. The preferred embodiment uses only the immediately adjacent pixels for inspection. A plurality of graylevel values are depicted by a plurality of bars 16, 17, 18, 19, and 21. The darkest pixel depicted in FIG. 2, bar 12, is at the same position in the representation of the image as bar 18. Bar 18 thus retains the graylevel value of bar 12 (FIG. 2). The position of bar 17 corresponds to bar 14 (FIG. 2). Neighbor bar 12 (FIG. 2) has the lowest graylevel value so bar 17 is given the same graylevel value as bar 12 (FIG. 2). Likewise bar 19, corresponding to bar 13 (FIG. 2), also receives the same graylevel value as bar 12 (FIG. 2). Thus three bars 17, 18, and 19 have the graylevel value of bar 12 (FIG. 2) which represents the darkest pixel in the area. Bar 16 which corresponds to bar 22 (FIG. 2) gets the graylevel value of bar 14 (FIG. 2). Similarly bar 21 is given the value of bar 13 (FIG. 2). The net result is to preserve the variations in graylevel value, but to enlarge the area of the dark portions.

Figure 5:
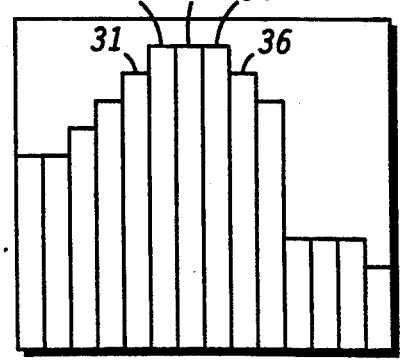
FIG. 5 shows FIG. 3 following a dilate operation.

FIG. 5 shows the portion of the image slice depicted in FIG. 3 following a graylevel morphological dilation. The graylevel morphological dilation serves to expand the area of the lightest portions of the representation of the image while preserving the relative brightness of other parts of the representation of the image. The graylevel morphological dilation is similar to the graylevel morphological erosion except that the lightest graylevel value is selected. In this graph the relative graylevel values are represented by a plurality of bars 31, 32, 33, 34, and 36. Bars 32, 33, and 34 have the same graylevel value as bar 27 (FIG. 3), their brightest neighbor in the original image slice. Likewise bar 31 receives the graylevel value of bar 26 (FIG. 3), and bar 36 is given the value of bar 28 (FIG. 3).

The technique described in FIG. 2 to 5 is applied to an entire image. This results in images which can be accurately registered to another. If the workpiece is defect free the images, every dark region and every bright region will coincide. Variations in the environment surrounding the workpiece, however, produce images which differ in overall brightness. To accurately compare the graylevels of two images, the representations of the images must be adjusted so that their overall brightness is the same. In a preferred embodiment of this invention, matching of brightness levels is achieved by further adjusting or mapping the values of the graylevel of each pixel of one image based on a comparison of the mean brightness level of the two images. Other embodiments use techniques such as adjustment of exposure times, video amplifier gain or emulsion speeds to match the brightness of the representations of the images.

Figure 6:
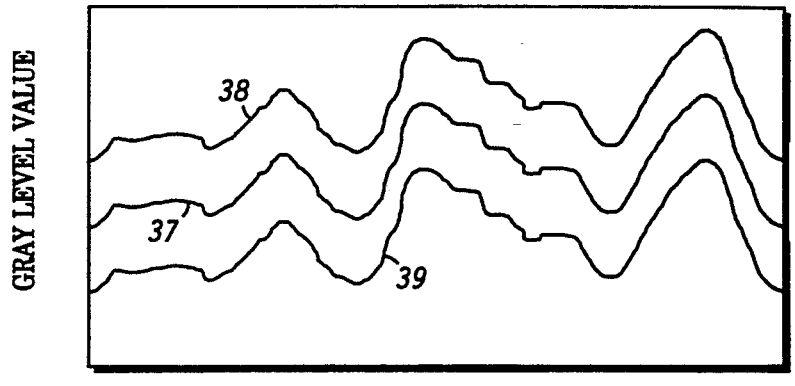
FIG. 6 shows FIG. 1 with differing brightness levels.

FIG. 6 shows the image slice represented in FIG. 1 with a plurality of brightness levels. A taught image slice of average brightness is represented by a graph of a plurality of graylevels 37, which are similar to graylevels 15 (FIG. 1). For explanatory purposes both a light run image and a dark run image are described even though only a single run image is typically used for each inspection. A relatively bright run image slice is represented by a graph of a plurality of graylevels 38. A relatively dark run image slice is represented by a graph of a plurality of graylevels 39. Mapping of the representation of the image brightness to remove this variation of brightness requires that the mean brightness level of both the taught image and the run image be determined. Graylevels 38 and 39 are then mapped by a linear scaling so the mean brightness level of both is the same as the mean value of taught image slice graylevels 37. A linear scaling of graylevel values serves to adjust the graylevel values which differ from the mean in proportion to their brightness levels. The preferred embodiment of this invention uses a graylevel histogram analysis to determine the mean brightness levels of the run image. Run image slice graylevels 38 and 39 are then mapped based on a comparison of the mean brightness of the taught image to that of the run image. An alternative embodiment of the present invention applies a mapping to the taught image, scaling graylevels 37 to match the desired run image graylevels. The graylevel histogram comprises a graph having the graylevels found in the representation of the image plotted along the abscissa. The number of pixels having a particular graylevel is plotted along the ordinate.

Figure 7:
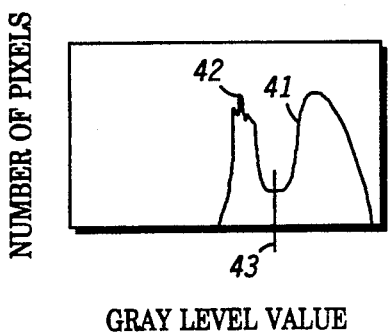
FIG. 7 is a histogram characterizing part of FIG. 6.

FIG. 7 depicts a first graylevel histogram characterizing the relatively bright run image slice represented by graylevels 38 (FIG. 6). The graylevel histogram characterizes the image as comprising a high concentration of bright pixels 41, a high concentration of dark pixels 42 and a minima between the two concentrations of pixels. A bar 43 is drawn at the graylevel corresponding to the minima to help illustrate the relative graylevels of the minima and corresponding minimums described below. Bar 43 indicates the minima in the graylevel histogram. This graylevel is selected as being the mean brightness of the run image and is used as a scale factor to map graylevels 38 to the brightness of graylevels 37.

Figure 8:
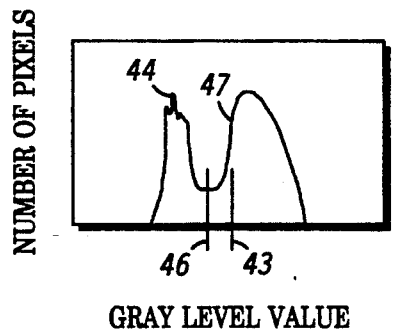
FIG. 8 is a histogram characterizing another part of FIG. 6.

FIG. 8 depicts a second graylevel histogram characterizing the brightness of the taught image slice represented by graylevels 37 (FIG. 6). The graylevel histogram characterizes the image as comprising a high concentration of bright pixels 47, a high concentration of dark pixels 44 and a minima between the two concentrations of pixels. The minima is marked by a bar 46. This graylevel value is selected as being the mean brightness of the image. Bar 43 is derived from the bright run image depicted in FIG. 7. The position of bar 43 is compared with the position of bar 46, derived from the taught image. This comparison shows the relative change of graylevel required to produce images having equivalent brightness. Either image may be mapped to achieve this equivalence. In the preferred embodiment, graylevels 38 (FIG. 6) representing the bright run image are mapped such that bar 43 coincides with bar 46. This mapping has the effect of decreasing the values of graylevels 38 (FIG. 6) to compensate for the effect of variations in run image brightness.

Figure 9:
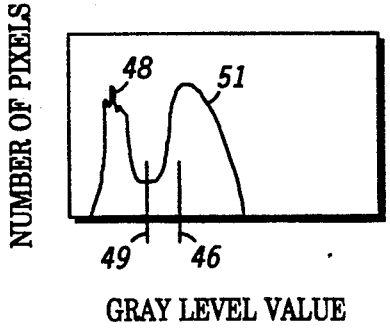
FIG. 9 is a histogram characterizing a third part of FIG. 6.

FIG. 9 depicts a third graylevel histogram characterizing the relatively dark run image slice represented by graylevels 39 (FIG. 6). The graylevel histogram characterizes the image as comprising a high concentration of bright pixels 51, a high concentration of dark pixels 48 and a minima between the two concentrations of pixels. A bar 49 marks this minima. Comparison of bar 49 derived from a dark run image, with bar 46 derived from a moderately bright taught image illustrates the relative change required to produce images having equivalent brightness. In a fashion similar to bar 43, the graylevel marked by bar 49 is selected as being the mean brightness of the image and is used as a scale factor to map graylevels 39 (FIG. 6) to the brightness of graylevels 37 by a linear scaling. This linear scaling has the effect of increasing the values of graylevels 39 (FIG. 6) to compensate for the effect of variations in brightness of the run image.

FIG. 10 is a representation of the comparative graylevels of two image slices after adjustment of the graylevel values and relaxation as described above. A taught image slice 52 is compared with a run image slice 53. For illustration the brightness of run image slice 53 has been slightly decreased. A plurality of dark defects 54 and a plurality of light defects 56 are identified by large differences in brightness between taught image slice 52 and run image slice 53. In a preferred embodiment of the present invention, the graylevel values of the taught image and the run image are compared by algebraically subtracting the respective graylevel values at each pixel location to produce a representation of a composite image in a computer memory. Other embodiments of the present invention use analog video comparator circuits or superimpose positive and negative photographic images to compare the two images and produce a representation of a composite image.

FIG. 11 depicts a slice of a representation of a composite image which represents the difference between the graylevels of the two images represented in FIG. 10. An average graylevel 57 results from the subtraction of the taught image slice and the run image slice. A bright threshold 58 and a dark threshold 59 define a predetermined range of acceptable graylevels and are used to separate minor processing variations from actual defects. Bright threshold 58 and dark threshold 59 are determined experimentally based on inspection of sample workpieces. Bright defects 56 extend above bright threshold 58 and dark defects 54 extend below dark threshold 59. Bright defects 56 have widths 62 measured at bright threshold 58. Dark defects 54 have widths 61 measured at dark threshold 59. A feature erode applied to bright defects 56 has the effect of reducing the size of the bright areas by the predetermined minimum defect size. Bright defects 56 having width 62 less than this predetermined minimum defect size are removed. The feature erode is similar to the erode operation detailed in FIG. 2 and 4, except that the erode is applied to bright areas rather than to dark areas as in FIG. 2 and 4. A similar feature dilate operation removes dark defects 54 having width 61 less than the predetermined minimum defect size. The result is an image slice which consists entirely of bright defects 56 and dark defects 54 which are larger than a predetermined minimum defect size. The defects are now identified by recording locations of bright defects 56 and dark defects 54 for later analysis.

By now it should be apparent that the present invention provides a method of image processing for visually inspecting a workpiece. The method is based on comparing the brightness at each location within an image of the workpiece to the equivalent location within an image of an idealized workpiece. The resulting inspection is insensitive to variations in absolute brightness, depending instead on local brightness differences between two images. The method according to the present invention can detect defects having no distinct edges. Finally this method can detect defects which are small enough that the representation of the image will show these small defects only as a single point of light or dark.

I claim:

1. A method for detecting defects which lack distinct edges, comprising:
   providing a graylevel representation of a taught image of a defect free workpiece;
   providing a graylevel representation of a run image of a workpiece being inspected, the run image revealing a defect which lacks distinct edges;
   registering the run image by mechanical and optical means to scale, rotation and spatial position of the taught image;
   refining the registration between the run image and the taught image by relaxation of the graylevel representation of at least one of the two images;
   providing a means to determine a mean brightness level of the run image;
   mapping values of the graylevel of each pixel of one image based on a comparison of the mean brightness level of the two images; and
   comparing the graylevel representations of the taught image with that of the run image to create a representation of a composite image which highlights the defect which lacks distinct edges.

2. The method for detecting defects which lack distinct edges of claim 1 further comprising:
   mapping the graylevel representation of the run image based upon the relative location of a local minima in a graylevel histogram which serves to characterize the taught image when compared to the location of an equivalent local minima in the graylevel histogram which serves to characterize the run image.

3. The method for detecting defects which lack distinct edges of claim 1 further comprising:
   mapping of the graylevel values using a linear scaling.

4. A method for detecting defects which lack distinct edges, comprising:
   providing a graylevel representation of a taught image of a defect free workpiece;
   providing a graylevel representation of a run image of a workpiece being inspected;
   registering the run image by mechanical and optical means to scale, rotation and spatial position of the taught image;
   refining the registration between the run image and the taught image by relaxation of the graylevel representation of at least one of the two images;
   providing a means to determine a mean brightness level of the run image;
   mapping values of the graylevel of each pixel of one image based on a comparison of the means brightness level of the two images;
   comparing the graylevel representations of the taught image with that of the run image to create a representation of a composite image which highlights defects including defects which lack distinct edges in the run image; and
   identifying defects by recording locations within the composite image which fall outside a predetermined range of acceptable graylevels.

5. The method for detecting defects which lack distinct edges of claim 4 further comprising:
   relaxing the graylevel of the run image with a combination of graylevel morphological erosion and graylevel morphological dilation.

6. The method for detecting defects which lack distinct edges of claim 4 further comprising:
   refining the registration between the run images and the taught image by relaxation of local brightness maxima and minima within the graylevel representation of the run image alone.

7. The method for detecting defects which lack distinct edges of claim 4 further comprising:
   refining the registration between the run image and the taught image by relaxation of local brightness maxima and minima within the graylevel representation of the taught image alone.

8. The method for detecting defects which lack distinct edges of claim 4 further comprising:
   eroding the representation of the composite image using a feature erode of defects having a brightness level which is greater than a predetermined range of acceptable graylevels so as to eliminate bright defects which are smaller than a predetermined size.

9. The method for detecting defects which lack distinct edges of claim 4 further comprising:
   dilating the representation of the composite image using a feature dilate of defects having a brightness level which si lower than a predetermined range of acceptable graylevels so as to eliminate dark defects which are smaller than a predetermined size.

10. A method for detecting defects which lack distinct edges, comprising:
    providing an image of a defect free workpiece;
    providing an image of a workpiece being inspected having a defect which lacks distinct edges;

adjusting values of a graylevel representation of the workpiece being inspected based on the relative location of a local minima in a graylevel histogram which serves to characterize the defect free workpiece image and an equivalent local minima found on the graylevel histogram which serves to characterize the image of the workpiece being inspected;

aligning the representation of the image of the workpiece being inspected to the defect free image by mechanical and optical means;

refining the alignment between the representation of the image of the workpiece being inspected and the representation of the image of the defect free workpiece by a relaxation of the graylevel representation of at lest one of the representations of the images;

comparing the graylevel representations of the images of the workpiece being inspected with the representation of the image of the defect free workpiece to create a representation of a composite image which highlights the defect which lacks distinct edges in the run image; and identifying defects including the defect which lacks distinct edges by recording locations within the composite image which are outside a predetermined range of acceptable graylevels.

11. A method for detecting defects which lack distinct edges, comprising:

providing a representation of an image of a defect free workpiece;

providing a representation of an image of a workpiece being inspected, the workpiece including a defect which lacks distinct edges;

registering the representation of the image of the workpiece being inspected by mechanical and optical means to scale, rotation and spatial position of the representation of the image of the defect free workpiece;

refining registration between the representation of the image of the workpiece being inspected and the representation of the image of the defect free workpiece by relaxation of a graylevel representation of the image of the defect free workpiece;

scaling values of the graylevel representation using a linear scale factor of the representation of the image of the workpiece being inspected based on the relative location of a local minima in graylevel histograms which characterize the representation of the image of the defect free workpiece and the representation of the image of the workpiece being inspected;

comparing the graylevel representations of the image of the defect free workpiece with that of the image of the workpiece being inspected thereby creating a representation of a composite image which highlights defects in the run image;

eroding the representation of the composite image to eliminate defects which are smaller than a predetermined size; and identifying defects, including the defect which lacks distinct edges by recording locations within the composite image which are outside a predetermined range of acceptable graylevels for the composite image.

* * * * *